(12) United States Patent
Martins

(10) Patent No.: US 9,943,289 B2
(45) Date of Patent: Apr. 17, 2018

(54) COLOR FLOW ULTRASOUND IMAGING

(71) Applicant: B-K MEDICAL APS, Herlev (DK)

(72) Inventor: Bo Martins, Rodovre (DK)

(73) Assignee: B-K Medical Aps, Herlev (DK)

( * ) Notice: Subject to any disclaimer, the term of this patent is extended or adjusted under 35 U.S.C. 154(b) by 566 days.

(21) Appl. No.: 13/904,200

(22) Filed: May 29, 2013

(65) Prior Publication Data
US 2014/0357999 A1 Dec. 4, 2014

(51) Int. Cl.
*A61B 8/08* (2006.01)
*A61B 8/00* (2006.01)
*A61B 8/06* (2006.01)

(52) U.S. Cl.
CPC .............. *A61B 8/5269* (2013.01); *A61B 8/06* (2013.01)

(58) Field of Classification Search
CPC .......... A61B 8/5269; A61B 8/06; A61B 8/463
USPC ......... 600/437, 441, 453–455; 382/128, 264, 382/274
See application file for complete search history.

(56) References Cited

U.S. PATENT DOCUMENTS

| | | |
|---|---|---|
| 5,327,894 A | 7/1994 | Thomas |
| 5,349,524 A | 9/1994 | Draft et al. |
| 5,349,525 A | 9/1994 | Dunki-Jacobs et al. |
| 5,524,629 A | 6/1996 | Mahony |
| 5,735,281 A * | 4/1998 | Rafter et al. .................. 600/458 |
| 6,760,486 B1 | 7/2004 | Chiao et al. |
| 6,979,295 B2 | 12/2005 | Dubberstein et al. |

OTHER PUBLICATIONS

Truong et al., Massively Parallel Provessor Array for Mid-/Back-end Ultrasound Signal Processing, IEEE Biomedical Circuits and Systems—BIOCAS, 2010, 4 sheets. www.ece.ucdavis.edu/vcl/pubs/2010.11.BioCAS/biocas2010_final.pdf.

* cited by examiner

*Primary Examiner* — Michael Rozanski
(74) *Attorney, Agent, or Firm* — Anthony M. Del Zoppo, III; Driggs, Hogg, Daugherty & Del Zoppo Co., LPA

(57) ABSTRACT

An ultrasound imaging system includes an ultrasound transducer array that receives a set of echo signals produced in response to an ultrasound signal traversing flowing structure in a portion of a tubular structure of an object or subject in an imaging field of view. An image processor processes the set of echo signals and generates a structure image. A color flow processor processes the set of echo signals and generates a color flow image indicative of a flow of the flowing structure in the portion of the tubular structure, including a flow direction and a flow magnitude of the flowing structure. A color flow corrector corrects the color flow image for at least one of color noise artifact or color flash artifact, producing a corrected color flow image. A video processor displays the structure image and the corrected color flow image superimposed over the structure image.

19 Claims, 6 Drawing Sheets

COLOR FLOW ULTRASOUND IMAGING

TECHNICAL FIELD

The following generally relates to ultrasound imaging and more particularly to color flow ultrasound imaging.

BACKGROUND

Ultrasound imaging provides information about the interior of a subject. For example, ultrasound imaging can be used to generate an image of an internal anatomical structure (e.g., a blood vessel, etc.) and/or a flow of an internal structure (e.g., flow of blood in a vessel, etc.). B-mode with color flow mapping (CFM) is one approach for visually displaying anatomical structure with color indicia representing flow of structure (direction and magnitude) superimposed thereover. Other indicia (e.g., arrows, etc.) may additionally or alternatively be displayed to convey the direction and/or magnitude of the flow.

For CFM of blood flow, a pulse-echo field is transmitted and oscillates along the beam. Blood cells traversing the lumen of the vessel interact with the pulse-echo field and produce signals with frequency components that are proportional to the axial velocity of the blood flow. These signals are used to estimate relative blood flow, determined based on a phase shift between returning frequencies and transmitted frequency, with positive shifts indicating blood is moving away from the transducer, and negative shifts indicating blood is moving towards the transducer. The resulting data has been superimposed over a corresponding B-mode image.

The ability to visualize deep flow, flow of low amplitude, and very slow flow has been affected by transmit and post-processing parameters such as a color gain and a color flow processor wall (or high-pass) filter cut-off frequency. The working range of these parameters has been based on the extent to which the generated color flow images include color noise artifact (non-flow (e.g., noise) perceived as flow and presented in color as flow) and/or color flash artifact (non-flow motion above the wall filter cut off frequency in a displayed frame). Both parameters have been provided as manually adjustable parameters by a user.

Color gain affects an energy of the transmitted ultrasound signal. Generally, a higher color gain level leads to more of the true flow signal being detected, but a higher color gain level may also lead to a lower amplitude, non-flow signal, such as noise, being falsely perceived as flow and presented in color as flow, e.g., color outside of the vessel. Color noise has been mitigated by having the user turn down the color gain level through trial and error until an acceptable level of color noise in the displayed image is reached. Unfortunately, decreasing the color gain level may also result in lost true signal and thus undetected blood flow.

The wall filter cut-off frequency is set to separate high-amplitude, low-frequency stationary signal of moving tissue (e.g., a vessel wall, the chest due to breathing, the heart beating, the subject moving his/her arm, etc.) or slight transducer motion from low-amplitude, higher-frequency signal of moving blood-cells. If set to high, then low flow signal is filtered, and true signal is lost. If set too low, then the moving tissue signal may create large areas of color in one frame, which is absent from other frames such as a next displayed frame (hence, a color flash). Unfortunately, color flashes can be visually annoying to the user and/or may even mask or obscure the true signal.

In view of at least the above, there is an unresolved need for other approaches for visualizing color flow images.

SUMMARY

Aspects of the application address the above matters, and others.

In one aspect, an ultrasound imaging system includes an ultrasound transducer array that receives a set of echo signals produced in response to an ultrasound signal traversing flowing structure in a portion of a tubular structure of an object or subject in an imaging field of view, an image processor that processes the set of echo signals and generates a structure image indicative of the portion of the tubular structure, a color flow processor that processes the set of echo signals and generates a color flow image indicative of a flow of the flowing structure in the portion of the tubular structure, including a flow direction and a flow magnitude of the flowing structure in the portion of the tubular structure, a color flow corrector that corrects the color flow image for at least one of color noise artifact or color flash artifact, producing a corrected color flow image, and a video processor that displays the structure image and the corrected color flow image superimposed over the structure image.

In another aspect, a method includes receiving a set of echo signals produced in response to an ultrasound signal traversing flowing structure in a portion of a tubular structure of an object or subject in an imaging field of view, processing the set of echo signals, thereby generating a structure image indicative of the portion of the tubular structure, processing the set of echo signals, thereby generating a color flow image indicative of a flow of the flowing structure in the portion of the tubular structure, including a flow direction and a flow magnitude of the flowing structure in the portion of the tubular structure, correcting the color flow image for at least one of color noise artifact or color flash artifact, producing a corrected color flow image, and displaying the structure image and the corrected color flow image superimposed over the structure image.

A computer readable storage medium is encoded with computer readable instructions, which, when executed by a processor, cause the processor to: receive a set of echo signals produced in response to an ultrasound signal traversing flowing structure in a portion of a tubular structure of an object or subject in an imaging field of view, process the set of echo signals, thereby generating a structure image indicative of the portion of the tubular structure, process the set of echo signals, thereby generating a color flow image indicative of a flow of the flowing structure in the portion of the tubular structure, including a flow direction and a flow magnitude of the flowing structure in the portion of the tubular structure, correcting the color flow image for at least one of color noise artifact or color flash artifact, producing a corrected color flow image, and displaying the structure image and the corrected color flow image superimposed over the structure image.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
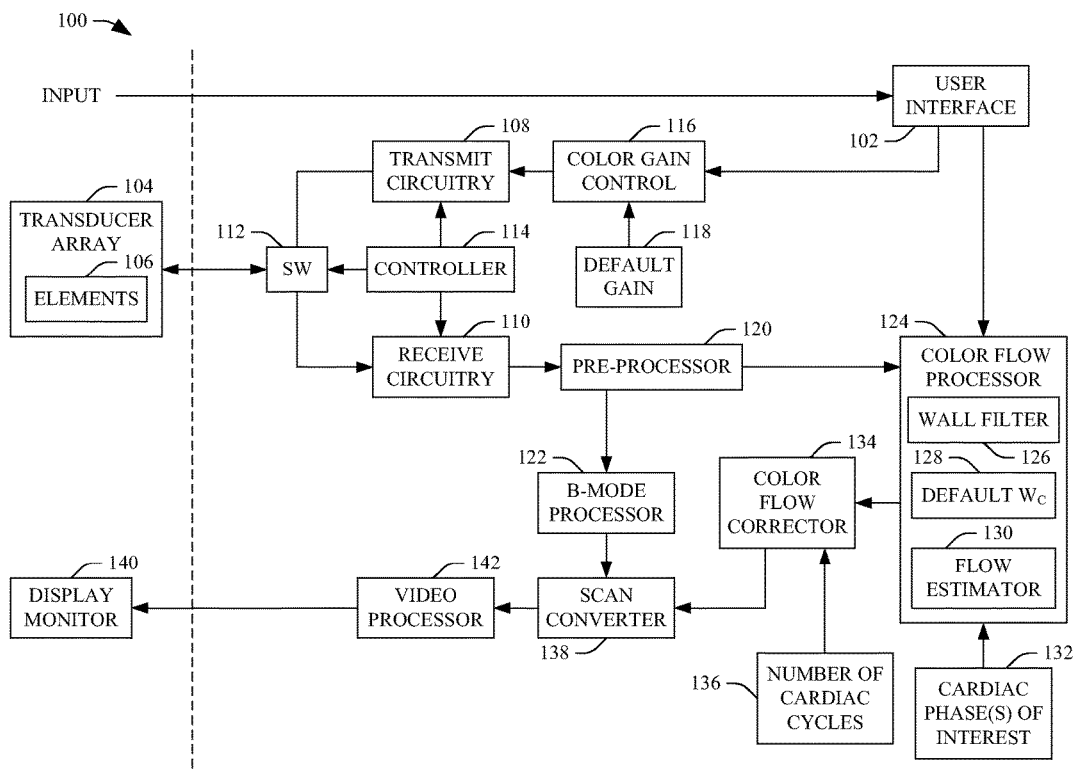
FIG. 1 illustrates an example ultrasound imaging system including a color flow corrector that mitigates at least one of color noise or color flashes in color flow images.

The following describes an ultrasound color flow image processing approach that mitigates color noise and/or color flashes associated with higher color gain and/or lower wall filter cut off frequency settings. Initially referring to FIG. 1, an example ultrasound imaging system 100 is illustrated.

A user interface (UI) 102 includes one or more input devices (e.g., a button, a knob, a slider, a touch pad, etc.) and/or one or more output devices (e.g., a display screen, lights, a speaker, etc.). The input and output devices allow a user to communicate with the system 100. For example, an input may identify and/or invoke a mode of operation, a color gain level, a wall filter cut off frequency, a set of color flow image filters to utilize, and/or other information.

A transducer array 104 includes an array of transducer elements 106, which are configured to transmit ultrasound signals that traverse a scan field of view and detect echo signals, which, generally, are produced in response to an interaction between the transmitted ultrasound signals and structure (e.g., flowing blood cells, organ cells, etc.) in the scan field of view, and generates radio frequency (RF) signals indicative thereof. The array 104 can be linear, curved, and/or otherwise shaped, fully populated or sparse, etc.

Transmit circuitry 108 generates a set of pulses that are conveyed to the transducer array 104, which excites transducer elements 106, causing the elements 106 to transmit the ultrasound signals. Receive circuitry 110 receives RF signals generated by the transducer array 104. Optionally, the receive circuitry 110 pre-processes the RF signals. A switch (SW) 112 switches the system 100 between transmit and receive operations. A controller 114 controls one or more of the transmit circuitry 108, the receive circuitry 110 or the switch 112.

A color gain control 116 determines a color gain level for the transmit circuitry 108. In the illustrated embodiment, the color gain can be set based on a default gain 118 and/or a signal from the UI 102 indicative of a user input gain level. The UI 102 can be used to vary the color gain while the system 100 displays images. As described in greater detail below, the system 100 corrects for color gain artifact and, thus, a higher color gain level can be used, relative to a configuration in which the color gain artifact is not corrected.

A pre-processor 120 pre-processes the RF signals. Examples of such pre-processing include, but are not limited to, conversion of analog RF signals to digital signals, demodulation, decimation, and/or other pre-processing.

A B-mode processor 122 processes the pre-processed data and generates B-mode images, which, generally, include a sequence of focused, coherent echo samples along focused scanlines of a scanplane. The B-mode processor 122 may also be configured to process the scanlines to lower speckle and/or improve specular reflector delineation via spatial compounding, and/or perform other processing such as FIR filtering, IIR filtering, edge enhancement, etc.

A color flow processor 124 processes the pre-processed data and generates color flow images.

The color flow processor 124 includes a wall filter 126. The wall filter 126 employs a predetermined default cut off frequency 128 and/or a cut off frequency identified from a signal from the UI 102 indicative of a user input cut off frequency value. The UI 102 can used to vary the cut off frequency while the system 100 displays images. As described in greater detail below, the system 100 corrects for color flash artifact and, thus, a lower wall filter cut off frequency can be used, relative to a configuration in which the color flash artifact is not corrected.

The color flow processor 124 further includes a flow estimator 130 that determines a magnitude and a direction of flow, using color flow mapping, vector flow imaging, and/or other approaches. The flow estimator 130 can estimate flow for one or more particular cardiac phase(s) of interest 132. The phase(s) of interest 132 can be a default and/or identified from a signal from the UI 102 indicative of a user input. An example approach for determining a systolic peak phase is described in patent application Ser. No. 13/838,329 to Martins et al., filed Mar. 15, 2013, entitled "DOPPLER ULTRASOUND IMAGING," which is incorporated by reference herein in its entirety.

In a variation, an ECG gating signal can be used to identify data corresponding to a particular cardiac phase. In this instance, this signal can be acquired through an ECG monitor, which acquires, simultaneously with data acquisition, the ECG gating signal. The ECG gating signal can be mapped to each other through time stamp, a field (e.g., the header) of the acquired data, and/or otherwise. In a variation, another approach can be used to determine the ECG and/or other cardiac gating signal, and/or other gating signal.

Figure 2:
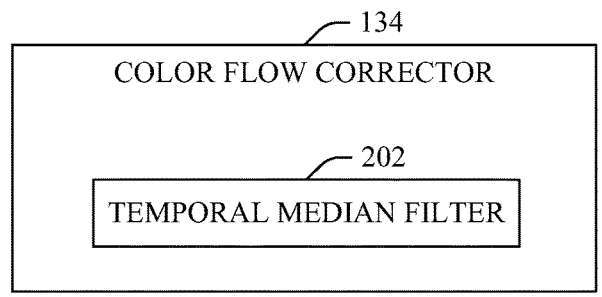
FIG. 2 illustrates an example in which the color flow corrector includes a temporal median filter.

A color flow corrector 134 corrects the color flow images output by the color flow processor 124 for color noise and/or color flashes. In one non-limiting example, e.g., as shown in FIG. 2, the color flow corrector 134 includes a temporal median filter 202, which determines a median value for individual pixels or samples (i,j) of a set of color flow images. In the illustrated embodiment, the number of images is determined based on a default number of cardiac cycles 136. In other instance, another motion, for example, the respiratory motion cycle and/or other motion cycle is used.

For example, in one instance, the temporal median filter 202 receives N color flow images (e.g., current image, image from 1 second ago, image from 2 seconds ago, . . . ) corresponding to a same phase point in the cardiac cycle, determines a median value for each pixel across the color flow images, and generates a color flow image in which each pixel represents the median pixel value. The majority of corresponding pixels across the color flow images will not include color noise or color flash, and, thus, the generated color flow image will have no or reduced color noise and/or color flash artifact.

Figure 3:
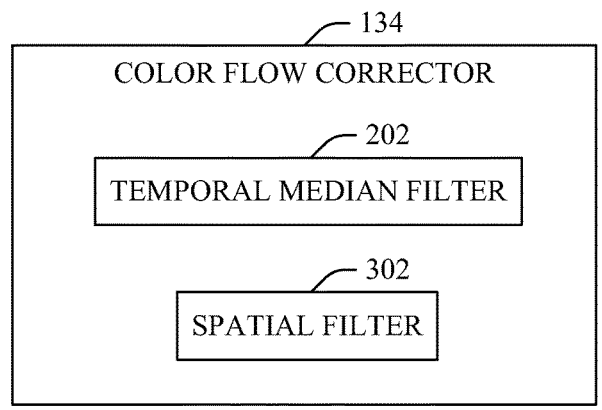
FIG. 3 illustrates an example in which the color flow corrector includes a temporal median filter and a spatial median filter.

Briefly turning to FIG. 3, a variation of the color flow corrector 134 includes the temporal median filter 202 and a spatial filter 302. In one instance, the spatial filter 302 includes a spatial median filter, which is well-suited for instances in which the number of cardiac cycles 136 is lower and color noise may pass through the temporal median filter 202. In this instance, a spatial filter 302 such as a 3×3, a 5×5, etc. filter is applied to each pixel, where, e.g., the pixel of interest is the center pixel. Residual color noise and/or color flash is mitigated. The median filter, generally, removes color dots along a thin line (small vessel).

In another instance, the spatial filter 302 includes steerable wavelets, which may reduce residual color noise. The steerable wavelets may be applied with a quantization step in the wavelet domain. The steerable wavelets filter connects color dots along a line. An example of steerable wavelets is given by Simoncelli's steerable pyramid. Generally, the steerable pyramid is a linear multi-scale, multi-orientation image decomposition front-end image-processing algorithm. An example of a steerable pyramid transformation is discussed in Unser et al., "Steerable Pyramids and Tight Wavelet Frames in $L_2(Rd)$," IEEE Trans. Image Processing, 20(10):2705-2721, October 2011.

Figure 4:
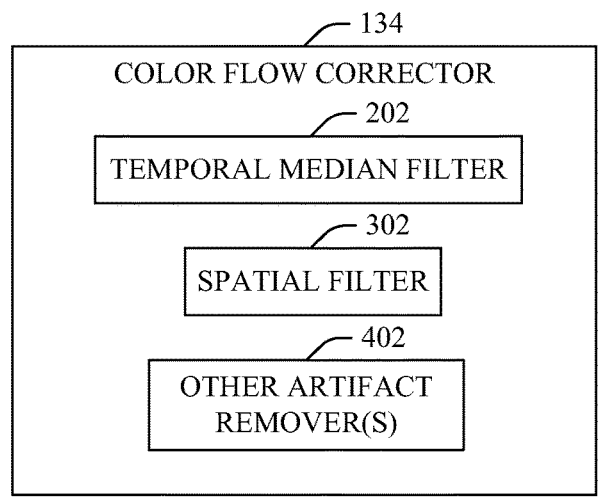
FIG. 4 illustrates an example in which the color flow corrector includes a temporal median filter, a spatial median filter, and other color sample processing component.

Briefly turning to FIG. 4, another variation of the color flow corrector 134 includes the filter 202, the filter 302 and/or one or more other color noise and/or color flash removers 402. Returning to FIG. 1, the configuration, 202, 302 or 402, can be based on the default number of cardiac cycles 136 and/or a user provided number of cardiac cycles. As described below, in another instance, motion detection can be utilized to determine which configuration 202, 302, or 402 to use, and/or the number of cardiac cycles.

Returning to FIG. 1, it is to be appreciated that the color flow corrector 134, relative to a configuration of the system 100 in which the color flow corrector 134 is omitted, allows for an increased working range for color gain level and/or the wall filter cut-off frequency since artifacts introduced thereby are mitigated through the color flow corrector 134. Through cardiac gating, data from a same phase point but different times are filtered, which allows for preserving the correct display of speed of flow in the different phase of the cardiac cycle, and results in images suitable for deep flow, weak flow, and/or slow flow imaging.

A scan converter 138 scan converts the B-mode and color flow images. This includes, for example, processing them to generate data for display, for example, by converting the data to the coordinate system of a display monitor 140. The scan converter 138 can be configured to employ analog and/or digital scan converting techniques.

A video processor 142 visually presents the B-mode images and the color flow images, for example, superimposed over the B-mode images through a graphical user interface (GUI) displayed through the display monitor 140. As discussed herein, the flow magnitude and direction information can be presented through various indicia such as, but not limited to, color, gray-scale, graphical vectors, flow lines and/or particles, animation, and/or other indicia.

It is to be appreciated that the color flow corrector 134 can be implemented through one or more hardware processors (e.g., a microprocessor, a central processing unit, etc.) executing one or more computer readable instructions encoded or embedded on computer readable storage medium (which does not include transitory medium), such as physical memory or the like. Additionally or alternatively, the one or more processors can execute at least one instruction(s) carried by transitory median such as a carrier wave, a signal, etc.

Figure 5:
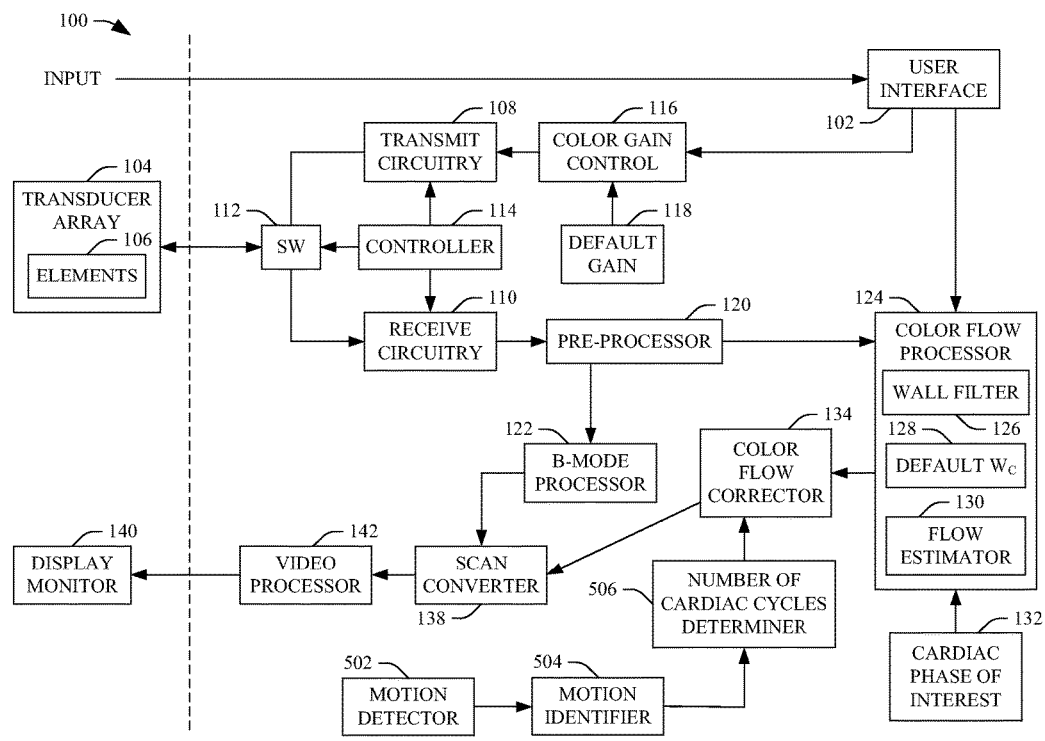
FIG. 5 illustrates a variation of the ultrasound imaging system of FIG. 1 in which detected motion is used to determine the number of color flow images processed by the color flow corrector to correct a color flow image.

FIG. 5 illustrates a variation of FIG. 1. In this variation, a motion detector 502 detects motion in the imaging field of view, and a motion identifier 504 determines whether the detected motion is motion related to non-flow structure or flowing structure. A number of cardiac cycles determiner 506, in response to the motion being identified as non-flow structure, reduces the number cardiac cycle used by the color flow corrector 134 (e.g., by the temporal median filter 202 of FIG. 2) to correct for color noise and/or color flash. The reduction can be based on a predetermined level of motion and may vary based on the level of the motion. The number of cardiac cycles determiner 506, in response to the motion being identified as flowing structure, returns the number cardiac cycle back to or maintains the default or user identified number of cardiac cycles. In either case, the color flow corrector 134 can employ the filter configuration 202, 302, or 402 of FIG. 2, 3, or 4.

Figure 6:
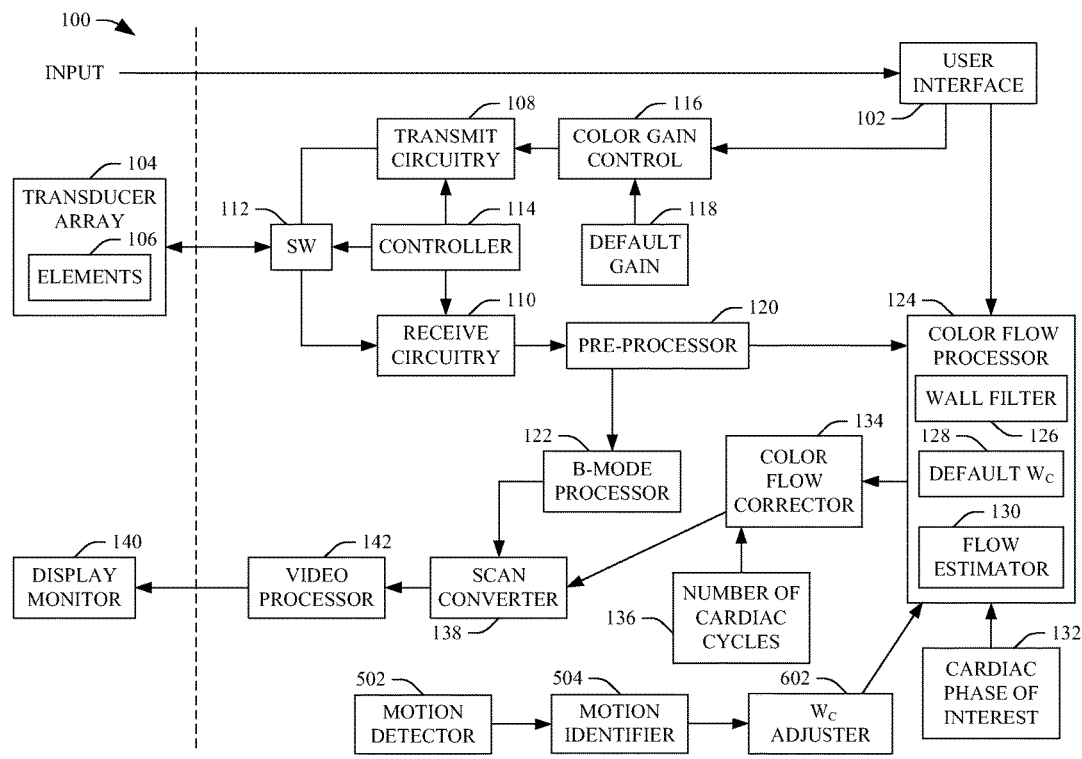
FIG. 6 illustrates a variation of the ultrasound imaging system of FIG. 1 in which detected motion is used to determine a wall filter cut off frequency.

FIG. 6 illustrates a variation of FIG. 1. In this variation, the motion detector 502 detects motion, and the motion identifier 504 determines whether the detected motion is motion related to non-flow structure or flowing structure. A cut off frequency ($W_c$) adjuster 602 dynamically increases the cut off frequency of the wall filter 126, in response to the motion being identified as non-flow structure. The increase can be based on a predetermined level of motion and may vary based on the level of the motion. The cut off frequency ($W_c$) adjuster 602 dynamically decreases, returns or maintains the cut off frequency of the wall filter 126, in response to the motion being identified as flowing structure. The decrease can be based on a predetermined level of motion and may vary based on the level of the motion. In either case, the color flow corrector 134 can employ the filter configuration 202, 302, or 402 of FIG. 2, 3, or 4.

Figure 7:
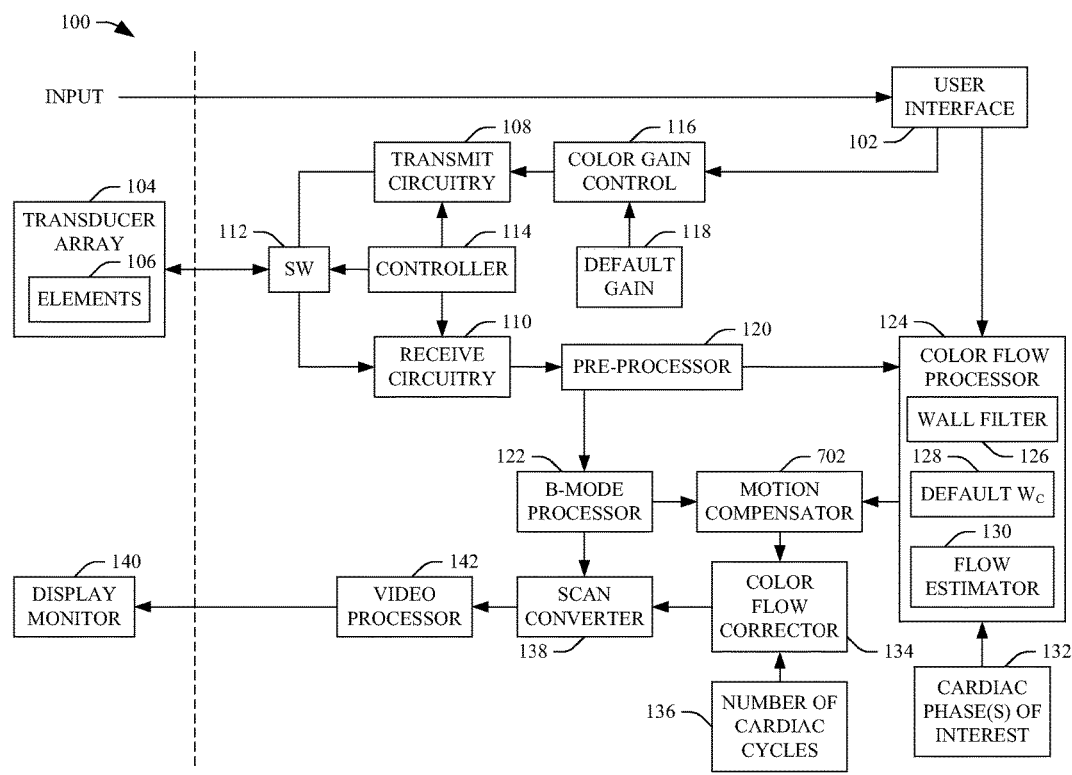
FIG. 7 illustrates a variation of the ultrasound imaging system of FIG. 1 in which the color flow image is motion compensated prior to correction.

FIG. 7 illustrates a variation of FIG. 1. In this variation, a motion compensator 702 compensates the color flow images prior to color flow correction. An example of a suitable non-limiting motion compensation approach is described in patent application Ser. No. 13/812,883 to Martins, filed Jan. 29, 2013, entitled "MOTION-COMPENSATED PROCESSING," which is incorporated by reference herein in its entirety. In this example, B-mode images from the same steering angle as the current B-mode image are aligned with the current B-mode image, and the motion compensator 702 determines how much the image has moved over the entire image (i.e., an image to image comparison), and motion compensates the color images based thereon. The color flow corrector 134 can employ the filter configurations 202, 302, or 402 of FIG. 2, 3, or 4.

In yet another variation, the system 100 may include a combination of FIGS. 1, 5, 6 and/or 7, and/or other approach(s). For example, in a combination of FIGS. 5 and 6, where the detected motion is identified as flow motion, the number of cycles can be increased, the wall filter cut off frequency can be lowered, and the filter configuration 202 (temporal median filter only) can be employed. However, where the detected motion is identified as flow motion, the number of cycles can be decreased, the wall filter cut off frequency can be raised, and the filter configuration 302 (temporal median filter followed by the spatial median filter) can used.

Figure 8:
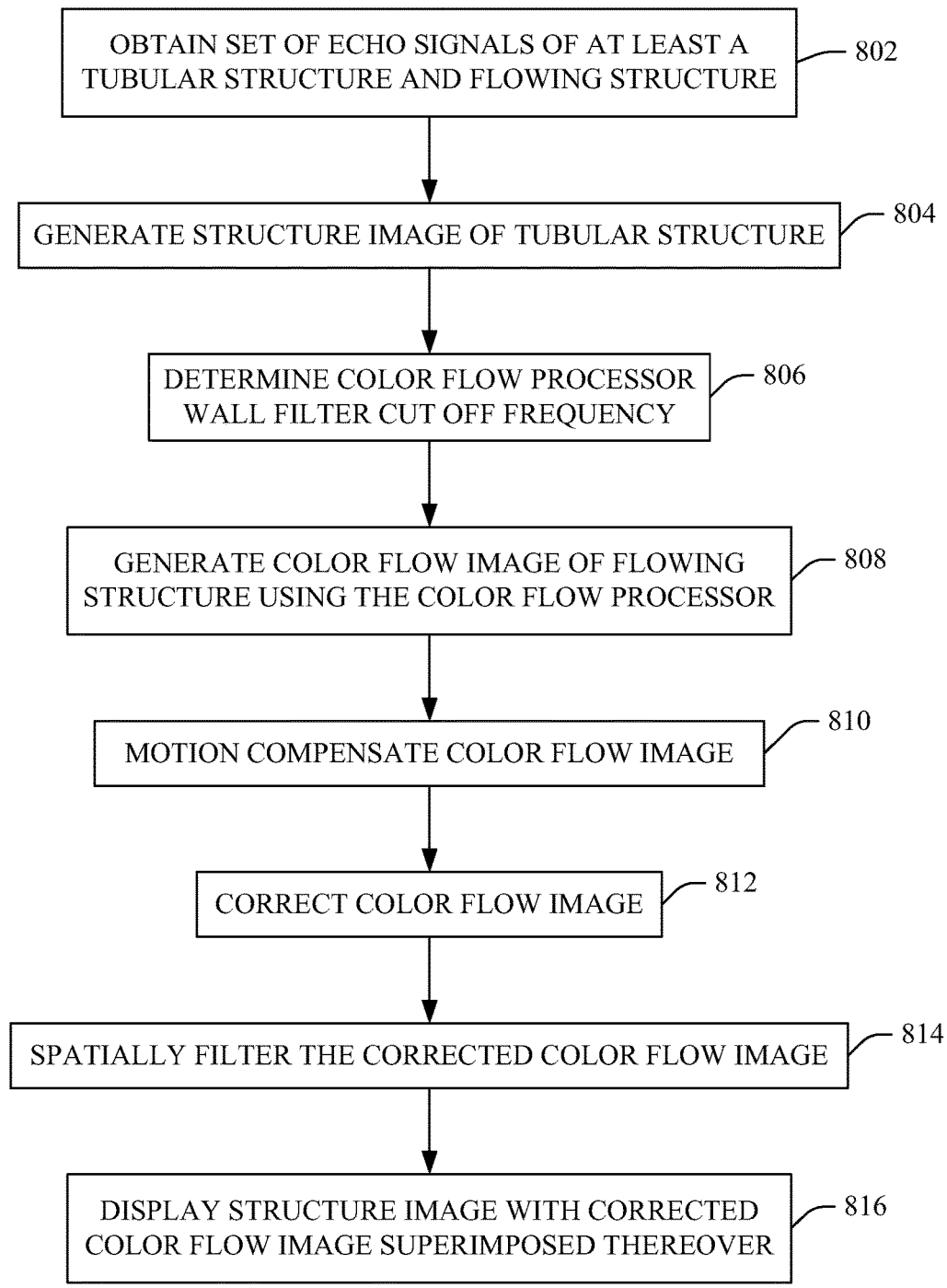
FIG. 8 illustrates a method for correcting for at least one of color noise or color flashes in a color flow images.

FIG. 8 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 802, a set of echo signals is obtained for an ultrasound scan of at least a tubular structure and flowing structure.

At 804, a structure image indicative of the tubular structure is generated based on the set of echo signals.

At 806, optionally, a wall filter cut off frequency of color flow processor is determined based on sensed motion. Additionally or alternatively, a predetermined fixed and/or a user adjustable wall filter cut off frequency is utilized.

At 808, a color flow image of the flowing structure is generated based on the set of echo signals using the color flow processor.

At 810, optionally, the color flow image is motion compensated.

At 812, the color flow image is corrected for at least one of color noise or color flash, as describe herein and/or otherwise, producing a corrected color flow image.

For example, a temporal median filter can be used to correct the color flow image. In this instance, the sensed motion can be used to determine how many color flow images are processed by the temporal median filter, and the color flow images can be selected based on motion gating and/or otherwise. As discussed herein, such filtering removes color noise and color flash artifacts.

At 814, optionally, the corrected color flow image is spatially filtered. As discussed herein, such filtering may remove residual color noise and color flash artifacts.

At 816, the structure image is displayed with the corrected color flow image superimposed thereover.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   an ultrasound transducer array that receives sets of echo signals produced in response to an ultrasound signal traversing flowing structure in a portion of a tubular structure of an object or subject in an imaging field of view;
   an image processor that processes the sets of echo signals and generates a structure image indicative of the portion of the tubular structure;
   a color flow processor that processes the sets of echo signals and generates color flow images indicative of a flow of the flowing structure in the portion of the tubular structure, including a flow direction and a flow magnitude of the flowing structure in the portion of the tubular structure, wherein the color flow images include at least one of color noise artifact or color flash artifact;
   a color flow corrector processor that corrects the color flow images for the at least one of the color noise artifact or the color flash artifact, producing corrected color flow images, wherein the color flow corrector processor includes a temporal median filter that corrects the color flow images for the at least one of the color noise artifact or the color flash artifact and produces the corrected color flow images by:
     receiving a plurality of color flow images of the color flow images, including color flow images with the at least one of the color noise artifact or the color flash artifact, wherein the received plurality of color flow images correspond to a same phase point in a motion cycle of the object or subject but different motion cycles; and
     generating the corrected color flow images with the received plurality of color flow images by computing a value at a pixel location of the corrected color flow images as a median value of values of the pixel location across the plurality of color flow images; and
   a video processor that displays the structure image and the corrected color flow images superimposed over the structure image.

2. The ultrasound imaging system of claim 1, wherein the motion cycle is a cardiac motion cycle and the same phase point corresponds to a peak systole.

3. The ultrasound imaging system of claim 1, further comprising:
   transmit circuitry that generates a set of pulses which are conveyed to the transducer array and which excite the transducer array to transmit the ultrasound signal; and
   a color gain control processor that determines a color gain level of the transmit circuitry, wherein the color gain level is adjustable and is set at a level which introduces color noise in the color flow images, and the color flow corrector processor corrects for the color noise introduced by the color gain level.

4. The ultrasound imaging system of claim 3, the color flow processor, comprising:
   a wall filter processor with a cut off frequency that filters low-frequency stationary signals of non-flow moving tissue and passes higher-frequency signal of flowing tissue, wherein the non-flow moving tissue includes tissue moving with a frequency higher than the cut off frequency, introducing color flashes into the color flow images, and the color flow corrector processor corrects for the color flashes.

5. The ultrasound imaging system of claim 4, further comprising:
   a motion detector that detects motion in the field of view; and
   a motion identifier processor that identifies whether the motion is motion of the non-flow moving tissue or motion of the flow of the flowing structure.

6. The ultrasound imaging system of claim 5, further comprising:
   a number of motion cycles determiner processor that determines a number of the plurality of the color flow images filtered by the temporal median filter and included in median value of pixel values, wherein the number of motion cycles determiner processor increases the number of the plurality of the color flow images filtered by the temporal median filter in response to the motion identifier processor identifying the detected motion as motion of the non-flow moving tissue and decreases the number of the plurality of color flow images filtered by the temporal median filter in response to the motion identifier processor identifying the detected motion as motion of the flowing structure.

7. The ultrasound imaging system of claim 6, the color flow corrector further comprising:
a spatial filter processor which spatially filters the temporally filtered color images.

8. The ultrasound imaging system of claim 5, further comprising:
a cut off frequency adjuster processor that adjust the cut off frequency of the wall filter processor, wherein the cut off frequency adjuster processor decreases the cut off frequency in response to the motion identifier processor identifying the detected motion as motion of the non-flow moving tissue, and increases the cut off frequency in response to the motion identifier processor identifying the detected motion as motion of the flowing structure.

9. A method, comprising:
receiving sets of echo signals produced in response to an ultrasound signal traversing flowing structure in a portion of a tubular structure of an object or subject in an imaging field of view;
processing the sets of echo signals, thereby generating a structure image indicative of the portion of the tubular structure;
processing the sets of echo signals, thereby generating color flow images indicative of a flow of the flowing structure in the portion of the tubular structure, including a flow direction and a flow magnitude of the flowing structure in the portion of the tubular structure;
receiving a plurality of the color flow images corresponding to a same phase point in a motion cycle of the object or subject but different motion cycles;
determining a median value for each pixel location across the plurality of the color flow images;
correcting the color flow images for at least one of color noise artifact or color flash artifact by generating corrected color flow images in which a value at a pixel location of the corrected color flow images is the median value for that pixel location; and
displaying the structure image and the corrected color flow images superimposed over the structure image.

10. The method of claim 9, further comprising:
determining a color gain level of transmit circuitry that transmits the ultrasound signal, wherein the color gain level introduces color noise into the color flow images;
receiving an input indicative of a change from a user in the color gain level; and
changing the color gain level based on the input.

11. The method of claim 9, further comprising:
wall filtering the sets of echo signals prior to generating the color flow image, wherein non-flow moving tissue includes tissue moving with a frequency higher than a cut off frequency of a wall filter which introduces color flashes into the color flow images.

12. The method of claim 11, further comprising:
detecting motion in the field of view; and
identifying whether the motion is motion of the non-flow moving tissue or motion of the flow of the flowing structure.

13. The method of claim 12, further comprising:
determining a number of the color flow images filtered by a temporal median filter and included in the median value of pixels values, wherein a number of motion cycles determiner increases the number of the color flow images filtered by the temporal median filter in response to a motion identifier identifying the detected motion as motion of the non-flow moving tissue and decreases the number of the color flow images filtered by the temporal median filter in response to the motion identifier identifying the detected motion as motion of the flowing structure.

14. The method of claim 13, comprising:
filtering, with a spatial filter, the color flow images filtered by the temporal median filter.

15. A non-transitory computer readable storage medium encoded with computer readable instructions, which, when executed by a processor, cause the processor to:
acquire, with an ultrasound transducer, ultrasound data;
process the ultrasound data, thereby generating color flow images;
correct the color flow images for at least one of color noise artifact or color flash artifact, by determining a median value for a same pixel location across the color flow images and producing corrected color flow images in which the same pixel location in the corrected color flow images is the median value for the same pixel location; and
display the corrected color flow images superimposed over a structure image.

16. The non-transitory computer readable storage medium of claim 15, wherein the color flow images are corrected by spatially filtering temporally filtered color flow images.

17. The non-transitory computer readable storage medium of claim 15, wherein the computer readable instructions, when executed by the processor, further cause the processor to: set a number of color flow images across a plurality of motion cycles to temporal filter based on detected motion.

18. The non-transitory computer readable storage medium of claim 15, wherein the computer readable instructions, when executed by the processor, further cause the processor to: set a wall filter cut off frequency based on detected motion.

19. The non-transitory computer readable storage medium of claim 15, wherein the computer readable instructions, when executed by the processor, further cause the processor to: motion-compensate the color flow images prior to correcting the color flow images.

* * * * *